United States Patent [19]

Cramer

[11] 4,025,570

[45] May 24, 1977

[54] PREPARATION OF 1,4-DIENES OF HIGH TRANS-ISOMER CONTENT

[75] Inventor: Richard David Cramer, Landenberg, Pa.

[73] Assignee: E. I. Du Pont de Nemours and Company, Wilmington, Del.

[22] Filed: Jan. 9, 1976

[21] Appl. No.: 647,993

[52] U.S. Cl. .................. 260/651 R; 260/654 R; 260/668 R; 260/680 R

[51] Int. Cl.² ................................. C07C 25/00

[58] Field of Search ... 260/680 R, 677 R, 683.15 D, 260/654 R, 651, 668 R

[56] References Cited

UNITED STATES PATENTS

| | | | |
|---|---|---|---|
| 3,306,948 | 2/1967 | Kealy | 260/680 |
| 3,565,967 | 2/1971 | Collette et al. | 260/680 |
| 3,679,772 | 7/1972 | Yoo | 260/677 R |

FOREIGN PATENTS OR APPLICATIONS

| | | | |
|---|---|---|---|
| 1,195,248 | 6/1970 | United Kingdom | 260/683.15 D |

Primary Examiner—Delbert E. Gantz
Assistant Examiner—Joseph A. Boska

[57] ABSTRACT

1,4-Dienes of high trans-isomer content are prepared by contacting ethylene with a 1,3-diene in the presence of a catalyst system comprising an organic solvent-soluble organonickel compound in which the nickel is zerovalent or divalent, a hydrocarbylaluminum chloride or bromide, and an aryl phosphinite. Optionally, the catalyst system may also contain a heteroorganoaluminum compound.

12 Claims, No Drawings

PREPARATION OF 1,4-DIENES OF HIGH TRANS-ISOMER CONTENT

BACKGROUND OF THE INVENTION

1. Field of the Invention

This invention relates to a process for preparing 1,4-dienes of high trans-isomer content.

2. Description of the Prior Art

Sulfur-curable elastomeric copolymers of $\alpha$-olefins with nonconjugated dienes are well known. Particularly important are terpolymers of ethylene, propylene and a nonconjugated diene comonomer having only one polymerizable double bond. Such terpolymers are known in the industry as EPDM elastomers. The nonconjugated diene comonomer generally is a 1,4-diene such as 1,4-hexadiene. Terpolymers of this type are finding increased use, for instance, in manufacture of molded automobile parts, transmission belts, hoses, and the like.

1,4-Dienes can be prepared by several processes, including the catalytic addition of an $\alpha$-olefin to a conjugated diene. U.S. Pat. No. 3,306,948, to Kealy discloses such a catalytic process. In this process the reactants are contacted in the presence of a catalyst made from at least two moles of an organometallic compound and one mole of a nickel compound containing at least one monodentate trivalent phosphorus ligand such as tributylphosphine. The organometallic compound can be, for example, an aluminum alkyl, an aluminum aryl, or an organoaluminum halide.

Although these processes give high yields of 1,4-dienes, they are deficient in that 1,4-diene products of low trans/cis isomer ratio, generally about 2:1 to at most 3:1, are obtained. Trans-1,4-dienes are much more desirable monomers for the EPDM elastomer synthesis because they give straight chain copolymers of good physical properties and sufficient unsaturation for sulfur vulcanization. The cis isomers give less unsaturated copolymers, thus rendering the copolymers less attractive commercially.

U.S. Pat. No. 3,565,967, to Collette and Su discloses a process for obtaining 1,4-dienes having a trans-cis-isomer ratio of at least 4:1. In this process ethylene is contacted with a 1,3-diene in the presence of a soluble zerovalent or divalent nickel compound, an organoaluminum chloride or bromide, and a tertiary phosphine

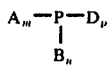

where A is the naphthyl radical, B is either a $C_1$-$C_6$ alkyl or the allyl radical, D is either the phenyl or a substituted phenyl radical, $m+n+p=3$, each of $m$ and $n$ independently can be 0, $m$ cannot be larger than 1, while $p$ cannot be smaller than 1, provided that when D is pentafluorophenyl, pentachlorophenyl, or tetramethylphenyl, then $p$ must be 1. Further increase in the trans/cis ratio can be obtained by the addition of an aluminum compound of the structure $(R_1)AlZ_b$ where $R_1$ is an alkyl, cycloalkyl or aryl radical having 1-12 carbons, and Z is $-OR_2$, $-N(R_3)(R_4)$ or $=N(R_5)$ where each of $R_2$, $R_3$, $R_4$, and $R_5$ can be an alkyl, cycloalkyl, aralkyl, or aryl radical having 1-12 carbons; when Z is $=N(R_5)$, $R_1$ can also be hydrogen; each of $a$ and $b$ is either 1 or 2, and the sum of $a+b$ is 3; except that when Z is $=NR_5$, each of $a$ and $b$ is 1, and $a+b$ is 2. The preferred phosphine, $(C_6H_5)_2PC_6F_5$, is relatively expensive and its use generally leads to slower reaction rates. It would be desirable to find a catalyst component which gives more rapid reaction and is less expensive than the tertiary phosphine.

SUMMARY OF THE INVENTION

It has now been discovered that 1,4-dienes of high trans-isomer content can be prepared by the process which comprises contacting ethylene with 1,3-diene of the formula

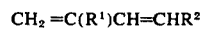

or

where
$R^1$ is hydrogen, methyl, ethyl or chlorine, and
$R^2$ is hydrogen, $C_1$-$C_{15}$ alkyl, $C_6$-$C_{12}$ aryl, or $C_7$-$C_{18}$ alkaryl, in the presence of a catalyst system which comprises
a. organic solvent-soluble organonickel compound in which the nickel is zerovalent or divalent,
b. hydrocarbylaluminum halide selected from the group consisting of hydrocarbylaluminum chlorides and hydrocarbylaluminum bromides, and
c. aryl phosphinite of the formula

where
$R^3$ and $R^4$, alike or different, are phenyl or substituted phenyl containing up to two substituents selected from the group consisting of $C_1$-$C_6$ alkyl, chlorine, bromine, iodine and fluorine, and
$R^5$ is $C_6$-$C_{12}$ aryl, or substituted $C_6$-$C_{12}$ aryl containing up to two substituents selected from the group consisting of $C_1$-$C_6$ alkyl, $C_1$-$C_6$ alkoxy, chlorine, bromine, iodine, fluorine, trifluoromethyl and di($C_1$-$C_6$ alkyl) amino.

It is preferred, because the trans/cis-isomer ratio of the 1,4-diene product is increased still further, to carry out the reaction in the presence of a heteroorganoaluminum compound of the formula

where
$R^6$ is $C_1$-$C_6$ alkyl, $C_3$-$C_6$ cycloalkyl, $C_7$-$C_{18}$ aralkyl, or $C_6$-$C_{12}$ aryl,
Z is $OR^7$, $-NR^8(R^9)$, or $=NR^{10}$,
where
$R^7$, $R^8$, $R^9$ and $R^{10}$, alike or different, are $C_1$-$C_6$ alkyl, $C_3$-$C_6$ cycloalkyl, $C_7$-$C_{18}$ aralkyl, or $C_6$-$C_{12}$ aryl,
$a$ is 1 or 2,
$b$ is 1 or 2, and
$a+b$ is 3,
except that when Z is $=NR^{10}$,
$a$ is 1,
$b$ is 1,
$a+b$ is 2, and
$R^6$ can also be hydrogen.

The terms "trans" and "cis" 1,4-dienes refer to the isomerism about the C-4/C-5 bond. Where $R^1$ in the starting 1,3-diene is hydrogen, a trans isomer has the configuration about the C-4/C-5 bond

Where R¹ is an atom or a group other than hydrogen, the trans isomer has the configuration

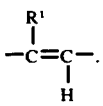

The cis isomer has the configuration

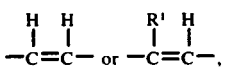

respectively.

The term "aryl" refers to a group derived from a hydrocarbon containing at least one 6-membered aromatic hydrocarbon ring by removal of a hydrogen atom from a ring carbon.

The term "alkyl" refers to a group derived from a saturated aliphatic hydrocarbon by removal of a hydrogen atom.

The term "cycloalkyl" refers to a group derived from a saturated alicyclic hydrocarbon by removal of a hydrogen atom.

The term "aralkyl" refers to a group derived from aliphatic hydrocarbon having at least one aromatic substituent by removal of an aliphatic hydrogen atom.

The term "alkaryl" refers to a group derived from aromatic hydrocarbon having at least one alkyl substituent by removal of an aryl hydrogen atom.

DETAILED DESCRIPTION OF THE INVENTION

In accordance with this invention 1,4-dienes having a trans/cis isomer ratio of at least about 4:1 are prepared by the addition of ethylene to 1,3-diene. Suitable 1,3-dienes for use in accordance with this invention include 1,3-butadiene, isoprene, 1,3-pentadiene, 1,3-hexadiene, chloroprene, 1,3-dodecadiene, 1,3-nonadecadiene, 4-phenyl-1,3-butadiene, and 5-phenyl-1,3-pentadiene. The preferred 1,3-diene for reaction with ethylene is 1,3-butadiene which gives as the product, 1,4-hexadiene, a very useful comonomer in the preparation of EPDM elastomers.

The reaction can be carried out either batchwise, semicontinuous or continuous. In the batch process, the reactants and the catalyst components are dissolved in an inert solvent, such as an aromatic or aliphatic hydrocarbon, or halogenated hydrocarbon. The concentration of 1,3-diene in a batchwise reaction can be varied virtually without limits, but it is convenient to use diene solutions which are about 1 to about 4 molar. In a continuous process the diene itself can serve as a solvent.

The reaction is carried out in the presence of a catalyst system containing an organic solvent-soluble organonickel compound in which the nickel is zerovalent or divalent. Suitable nickel compounds include nickel-(O)bis-(1,5-cyclooctadiene) complex, nickel tetracarbonyl, nickel-(O)(1,5,9-dodecadiene) complex, nickel-(O)(cyclooctatetraene) complex, nickel (II) acetylacetonate, nickel (II) cyclohexylbutyrate, dicrotyl-nickel (II), diallylnickel (II), dimethallylnickel (II), and crotyl-, allyl-, and methallyl-nickel (II) dichloride, dibromide, and diiodide. The preferred nickel compound is nickel(O)bis(1,5-cyclo-octadiene).

The nickel compound concentration generally is maintained within the range of about 0.00001 to about 0.01 mole per liter. Below the lower limit the reaction does not proceed at a satisfactory rate, while above the upper limit the reaction is difficult to control, and appreciable polymer formation is observed.

The catalyst system also contains a hydrocarbylaluminum chloride or bromide. Hydrocarbylaluminum halides which can be used in the process of this invention include alkylaluminum, arylaluminum, and aralkylaluminum halides. The organic radical usually has 1 to about 12 carbon atoms, the preferred number being 2 to about 6 carbon atoms. These preferred compounds are readily available at moderate cost and have high catalytic activity on a weight basis. Representative compounds include dialkylaluminum halides such as diethylaluminum chloride, dibutylaluminum chloride, diisobutylaluminum chloride and dipropylaluminum chloride; diarylaluminum halides such as diphenylaluminum chloride and dinaphthylaluminum chloride; diaralkylaluminum halides such as dibenzylaluminum chloride and di(p-methylbenzyl)-aluminum chloride; alkylaluminum dihalides such as ethylaluminum dichloride, propylaluminum dichloride and isobutylaluminum dichloride; arylaluminum dihalides such as phenylaluminum dichloride and naphthylaluminum dichloride; aralkylaluminum dihalides such as benzylaluminum dichloride and p-methylbenzylaluminum dichloride; and the corresponding dibromides. Usually, alkylaluminum dihalides are the most readily available and especially preferred compounds.

The amount of hydrocarbylaluminum halide present should be at least equimolar with the nickel compound. Although a large molar excess of the hydrocarbylaluminum halide can be present, e.g., about 100:1, no advantage is gained thereby. The preferred molar ratio of aluminum to nickel, at which the reaction is readily controlled, is about 3:1 to about 10:1. In general, an increase in the aluminum/nickel ratio gives increased conversions, but a lower trans/cis ratio.

The catalyst system also contains an aryl phosphinite of the formula

R³R⁴POR⁵ 

as defined above, which forms a stable complex with the organonickel compound. The ability of a phosphinite to form such a complex depends on several factors, including the phosphinite's basicity and steric effects. It has been found that phosphinites of the above formula satisfy all the requirements. Representative phosphinites include unsubstituted aryl diphenylphosphinites such as phenyl diphenylphosphinite,
2-naphthyl diphenylphosphinite,
1-naphthyl diphenylphosphinite and
4-biphenylyl diphenylphosphinite;

substituted aryl diphenylphosphinites such as 2-chlorophenyl diphenylphosphinite,
4-chlorophenyl diphenylphosphinite, 4-i-propylphenyl diphenylphosphinite,
2-methylphenyl diphenylphosphinite,
3-trifluoromethylphenyl diphenylphosphinite,
2-ethylphenyl diphenylphosphinite,
2-hexylphenyl diphenylphosphinite,
3-fluorophenyl diphenylphosphinite,
3-bromophenyl diphenylphosphinite,
3-iodophenyl diphenylphosphinite,
3-methylphenyl diphenylphosphinite,
3-i-propylphenyl diphenylphosphinite,
4-methoxyphenyl diphenylphosphinite,
2-methyl-4-methoxyphenyl diphenylphosphinite,
4-butoxyphenyl diphenylphosphinite,
4-(dimethylamino)phenyl diphenylphosphinite,
4-(diethylamino)phenyl diphenylphosphinite,
2-methyl-4-chlorophenyl diphenylphosphinite,
2,4-dimethylphenyl diphenylphosphinite,
2-methyl-4-methoxyphenyl diphenylphosphinite,
3,5-dichlorophenyl diphenylphosphinite,
4-hexyloxyphenyl diphenylphosphinite,
2-methyl-1-naphthyl diphenylphosphinite, and
2-chloro-1-naphthyl diphenylphosphinite;

and aryl di(substituted phenyl)phosphinites such as phenyl bis(2-methylphenyl)phosphinite,
phenyl bis(4-bromophenyl)phosphinite,
phenyl bis(2-methyl-4-chlorophenyl)phosphinite,
phenyl bis(4-i-propylphenyl)phosphinite,
phenyl bis(2,4-dimethylphenyl)phosphinite,
phenyl bis(4-hexylphenyl)phosphinite,
phenyl bis(4-fluorophenyl)phosphinite,
phenyl bis(4-iodophenyl)phosphinite,
2-chlorophenyl bis(4-chlorophenyl)phosphinite, and
2-naphthyl bis(4-chlorophenyl)phosphinite.

The preferred aryl phosphinites are substituted phenyl diphenylphosphinites.

In addition to the hydrocarbylaluminum halide, or as a replacement for part of the hydrocarbylaluminum halide present in the reaction medium, a heteroorganoaluminum compound of the formula $(R^6)_a AlZ_b$, as defined above, optionally can also be present in the solution. The presence of such a heteroorganoaluminum compound, which has a higher basicity than the hydrocarbylaluminum halide, further increases the trans/cis ratio of the 1,4-diene produced by the process of this invention. Representative heteroorganoaluminum compounds in which Z is -$OR^7$ include dialkylaluminum alkoxides such as diethylaluminum ethoxide, dimethylaluminum ethoxide and diisobutylaluminum methoxide; dialkylaluminum aryloxides such as diethylaluminum phenoxide and diisobutylaluminum phenoxide; dialkylaluminum aralkoxides such as dipropylaluminum benzyloxide and diethylaluminum benzyloxide; diarylaluminum alkoxides such as diphenylaluminum ethoxide and di(p-tolylaluminum) ethoxide; diaralkylaluminum alkoxides such as dibenzylaluminum ethoxide and dibenzylaluminum methoxide; alkylaluminum dialkoxides such as methylaluminum dipropoxide, and isobutylaluminum diisopropoxide; cycloalkylaluminum dialkoxides such as cyclohexylaluminum dimethoxide; arylaluminum dialkoxides such as phenylaluminum dimethoxide and p-tolylaluminum diethoxide; and aralkylaluminum dialkoxides such as benzylaluminum diethoxide and benzylaluminum dipropoxide.

Representative compounds in which Z is $-NR^8(R^9)$ include dialkylaluminum N,N-dialkylamides such as diethylaluminum N,N-dimethylamide, dibutylaluminum N,N-dimethylamide, dipropylaluminum N,N-diethylamide and dibutylaluminum N,N-diisopropylamide; alkylaluminum N,N,N',N'-tetraalkyldiamides such as ethylaluminum N,N,N',N'-tetraethyldiamide, and methylaluminum N,N,N',N'-tetramethyldiamide; cycloalkylaluminum N,N,N',N'-tetraalkyldiamides such as cyclohexylaluminum N,N,N',N'-tetramethyldiamide; arylaluminum N,N,N',N'-tetraalkyldiamides such as phenylaluminum N,N,N',N'-tetramethyldiamide and p-tolylaluminum N,N,N',N'-tetramethyldiamide; and aralkylaluminum N,N,N',N'-tetraalkyldiamides such as benzylaluminum N,N,N',N'-tetramethyldiamide and benzylaluminum N,N,N',N'-tetraethyldiamide.

Representative compounds in which Z is $=NR^{10}$ include, for example, alkylaluminum alkylimides such as ethylaluminum ethylimide, ethylaluminum methylimide, butylaluminum ethylimide and isopropylaluminum methylimide; alkylaluminum aralkylimides such as isopropylaluminum benzylimide and ethylaluminum benzylimide; cycloalkylaluminum alkylimides such as cyclohexylaluminum methylimide; arylaluminum alkylimides such as phenylaluminum methylimide and phenylaluminum ethylimide; aralkylaluminum arylimides such as benzylaluminum phenylimide and benzylaluminum p-tolylimide; alkylaluminum arylimides such as methylaluminum phenylimide, ethylaluminum phenylimide and isobutylaluminum phenylimide; and arylaluminum arylimides such as phenylaluminum phenylimide and p-tolyaluminum phenylimide. The preferred heteroorganoaluminum compounds are the dialkylaluminum alkoxides.

The amount of the heteroorganoaluminum compound used is based on the concentration of the hydrocarbylaluminum halide in the solution. Usually, the concentration of heteroorganoaluminum compound is chosen so that there are at least about 0.6 Z group present in solution for each three halogen atoms. It is not practical to increase the concentration of the heteroorganoaluminum compound beyond the ratio of about 1.2 Z for each halogen atom because the reaction rate is thereby unduly decreased. The preferred concentration range is about 0.2 to about 1 Z group for each halogen atom.

The aryl phosphinite is usually either premixed with the nickel compound or added separately. When the reaction is carried out batchwise, the hydrocarbylaluminum halide is usually added last. When a heteroorganoaluminum compound is employed, it is convenient to premix it with the hydrocarbylaluminum halide. The amount of aryl phosphinite present in the catalytic system should be about equimolar with the nickel compound. Although an excess quantity of aryl phosphinite can be present, it is undesirable because it can change the acidity of the medium to the extent that the addition reaction is impaired or prevented. A proper balance must therefore be maintained between the concentration of the aryl phosphinite and the acidic hydrocarbylaluminum halide.

The reaction is carried out within the temperature range of about $-20°$ to about $100°$ C. The most suitable temperature range is from about $0°$ to about $40°$ C since the isomer ratio can best be controlled under these conditions and the reaction rate is satisfactory. At higher temperatures, more polymeric material may be formed. Generally, formation of polymeric material cannot be completely avoided. It is possible, however, to keep it at a low level of 3 to 4%, or at most about 20% of the total product. So long as the total conversion is raised no higher than about 40–60%, formation of polymeric materials does not exceed these limits. Above this conversion range, not only is a higher proportion of polymeric material formed, but also other by-products often increase. The reaction is exothermic, and the reactor preferably is cooled to control the temperature.

The reaction is carried out at pressures from about atmospheric up to about 10,000 psig. The most suitable range for both the batch and continuous processes is about 15 to about 500 psig because good rates are obtained within this range over a wide range of temperatures. At pressures above 10,000 psig the reaction tends to proceed faster and may lead to more polymeric materials, while at pressures below atmospheric the reaction ratio is often too slow to be practical. In practice, a batch reactor is maintained under a constant ethylene pressure by leaving the ethylene supply lines open during the reaction. The amount of ethylene which is dissolved in the reaction medium depends on the partial pressure of ethylene gas above the solution. Ethylene which is consumed in the addition reaction is constantly replaced. In the continuous process it is advantageous to use pressures at the higher end of the preferred range with as short residence times as practical for the desired conversion of 1,3-diene.

Prior to the reaction, the reactor is swept with a dry inert gas. The addition of ethylene to the 1,3-diene is also carried out in a dry inert atmosphere. Because of its low cost and ready availability, nitrogen is the preferred inert gas. In a batch reactor a small amount of nitrogen may be present, its partial pressure usually being no more than about 10 psig. In a continuous reactor the nitrogen originally present is eventually completely displaced by the stream of ethylene.

When the reaction has reached the desired conversion level, the organoaluminum compounds present in the solution are decomposed by adding a compound having an active hydrogen, such as an alcohol, phenol, or even water. It is preferred to use an alcohol. The reaction mixture is distilled to separate the reaction products from the monomers and the catalyst. Alternatively, the reaction can be stopped by cooling to about −20° C, and the monomers can be removed at this low temperature by distillation at reduced pressure. In either case, the monomers can be recycled. When the reaction is stopped by cooling, the catalyst can also be recycled. It is usually necessary in such a case to add more organoaluminum compounds, while it is not necessary to replace the nickel compound, since it does not undergo decomposition in the reaction.

1,4-Dienes with a high trans-isomer content, which are prepared by the process of the present invention, are particularly useful in the preparation of ethylene/-propylene/unconjugated diene terpolymers (EPDM polymers), in which they supply vulcanization sites.

EXAMPLES OF THE INVENTION

The following examples illustrate the process of this invention. All parts and percentages are by weight and all degrees are Centigrade unless otherwise stated.

EXAMPLE 1

The nickel (O)bis(cyclooctadiene) use in this example was prepared by the reaction of nickel bis(acetylacetonate) with cyclooctadiene, butadiene, and aluminum triethyl as described by Collette and Su in U.S. Pat. No. 3,565,967.

The reaction of ethylene with 1,3-butadiene was carried out as follows:

The reaction vessel consisted of a glass lower section and a stainless steel upper section fitted with tubes through which reactants could be added to and products withdrawn from the glass section. The vessel was equipped with a stirrer and the two sections were clamped together using a gasket of Teflon fluorocarbon polymer. It was immersed in water at 26°, evacuated, and pressured to 30 psig with ethylene. Four solutions were delivered to the reactor: (1) 20% 1,3-butadiene in toluene at the rate of 81 ml per hr; (2) a 0.1 M solution of nickel(0)bis(cyclooctadiene) in toluene at the rate of 1 ml per hr; (3) a 0.1 M solution of phenyl diphenylphosphinite in toluene at the rate of 1 ml per hr; and (4) a toluene solution which was 1 M in ethylaluminum dichloride and 1.8 M in diethylaluminum ethoxide at the rate of 1 ml per hr. Ethylene was added continuously so that the total pressure within the reactor was maintained at 30 psig.

When 15 ml of liquid had accumulated in the reactor, liquid was withdrawn continuously at the rate of about 84 ml per hour to maintain the volume of solution in the reactor at 15 ml. The reaction was continued for 5 hours. About 1% of methanol was added continuously to the product as it discharged from the reactor to destroy the catalyst and arrest further reaction.

Periodic gas liquid chromatographic (GLC) analysis of the product was carried out on a ⅛ inch × 12 feet column of 20% cyanoethyl silicone (GE XE-60) on an 80–100 mesh diatomite support. The column was programmed for a rise in temperature from 35° to 50° over an 11-minute period, and it was then programmed to 200° at a rate of 40°/min. The helium flow rate was 40 ml/min. The analysis showed that up to 10% of the butadiene was converted to 1,4-hexadiene in which the ratio of trans-1,4-hexadiene to cis-1,4-hexadiene was 4.2:1 which is equivalent to a trans-isomer content of 81%.

EXAMPLE 2

Using the same equipment and the same general procedure as in Example 1, four solutions: (1) 20% 1,3-butadiene in toluene at the rate of 88 ml per hr; (2) 0.1 M nickel(O)bis(cyclooctadiene) in toluene at the rate of 0.9 ml per hr; (3) 0.1 M 2-chlorophenyl diphenylphosphinite in toluene at the rate of 0.9 ml per hr; and (4) a toluene solution 1 M in ethylaluminum dichloride and 1.8 M in diethylaluminum ethoxide at the rate of 0.9 ml per hr, were added simultaneously to the reactor at 25° and under ethylene at a total pressure of 30 psig.

The volume of liquid maintained in the reactor was 20 ml and reaction extended over 3 hr. Samples were analyzed by GLC analysis at 30 min intervals. The extent of conversion of butadiene to 1,4-hexadiene ranged from 12% to 25% and the trans-1,4-hexadiene/-cis-1,4-hexadiene ratio from 4.1/1 to 4.3/1.

EXAMPLE 3

Using the equipment and procedure of Example 1, four solutions: (1) 20% 1,3-butadiene in toluene at the rate of 47 ml per hr; (2) 0.1 M nickel(O)bis(cyclooctadiene) in toluene at the rate of 1.0 ml/hr; (3) 0.1 M phenyl diphenylphosphinite in toluene at the rate of 1.0 ml/hr; (4) a toluene solution which was 1 M in isobutylaluminum dichloride and 1.8 M in diethylaluminum ethoxide at the rate of 1 ml per hr, were added simultaneously to the reactor at 0° under ethylene at a total pressure of 30 psig.

The volume of liquid maintained in the reactor was 20 ml and the reaction extended over 4 hours. Samples were analyzed by GLC analysis at 30 min intervals. The extent of conversion of butadiene to 1,4-hexadiene ranged from 5% to 15% and the trans/cis-isomer ratio from 5.8/1 to 6.4/1.

EXAMPLES 4–13

A 30-ml glass reaction vessel containing a magnetized stirrer bar was purged with nitrogen, chilled to −80° and charged, under nitrogen, with reactants in the following sequence: (1) 10 ml of 20% 1,3-butadiene in toluene; (2) 0.1 ml of 0.066 M aryl diphenylphosphinite in toluene; (3) 0.2 ml of 0.033 M nickel(O)bis(cyclooctadiene) in toluene; and (4) 0.1 ml of a toluene solution that was 0.25 M in isobutylaluminum dichloride and 0.1 M in diethylaluminum ethoxide. The flask was immersed in liquid nitrogen to freeze the reaction mixture and evacuated. Twenty milliliters of ethylene gas was admitted, the reactor was immersed in a water bath at 30°, and additional ethylene was admitted at a pressure of 30 psig with stirring. After 30 minutes the valve through which ethylene was admitted was closed and the reaction mixture was chilled to −80°. The reactor was then opened and about 1 ml of methanol was added to arrest the catalyst. The reaction product was analyzed by GLC analysis. The specific aryl diphenylphosphinite used and the results are summarized in Table I.

TABLE I

| Example | Aryl Diphenylphosphinite | % Conversion (1,3-Butadiene to 1,4-Hexadienes) | 1,4-Hexadiene trans/cis Isomer Ratio |
|---|---|---|---|
| 4 | Phenyl diphenylphosphinite | 25 | 4.56 |
| 5 | 4-Isopropylphenyl diphenylphosphinite | 20 | 4.20 |
| 6 | 2-Methylphenyl diphenylphosphinite | 25 | 4.15 |
| 7 | 3-Trifluoromethylphenyl diphenylphosphinite | 20 | 4.33 |
| 8 | 2-Ethylphenyl diphenylphosphinite | 20 | 4.23 |
| 9 | 2-Chlorophenyl diphenylphosphinite | 25 | 5.13 |
| 10 | 3-Fluorophenyl diphenylphosphinite | 20 | 4.88 |
| 11 | 3-Methylphenyl diphenylphosphinite | 20 | 4.40 |
| 12 | 3-Isopropylphenyl diphenylphosphinite | 20 | 4.36 |
| 13 | 2-Naphthyl diphenylphosphinite | 20 | 4.06 |

EXAMPLES 14–16

The general procedure was that described for Examples 4–13 except that the toluene solution, 0.25 M in isobutylaluminum dichloride and 0.1 M in diethylaluminum ethoxide, was replaced with 0.1 ml of a toluene solution that was 0.15 M in isobutylaluminum dichloride. The results are summarized in Table II.

TABLE II

| Example | Aryl Diphenylphosphinite | % Conversion (1,3-Butadiene to 1,4-Hexadienes) | 1,4-Hexadiene trans/cis Isomer Ratio |
|---|---|---|---|
| 14 | 4-Chlorophenyl diphenylphosphinite | 20 | 4.19 |
| 15 | Phenyl diphenylphosphinite | 20 | 4.30 |
| 16 | 2-Chlorophenyl diphenylphosphinite | 20 | 4.94 |

EXAMPLE 17

A 30-ml glass reactor containing a magnetized stirrer bar was purged with nitrogen, chilled to −80° and charged, under nitrogen, with reactants in the following sequence: (1) 10 ml of 20% 1,3-butadiene in toluene; (2) 0.1 ml of 0.066 M phenyl diphenylphosphinite in toluene; (3) 0.2 ml of 0.033 M nickel bis(acetylacetonate) in toluene; and (4) 0.4 ml of a toluene solution which was 0.15 M in isobutylaluminum dichloride and 0.15 M in diethylaluminum ethoxide. The flask was immersed in liquid nitrogen to freeze the reaction mixture, and evacuated. Twenty milliliters of ethylene gas was admitted, the reactor was immersed in a water bath at 30°, and additional ethylene was admitted at a pressure of 70 psig with stirring. After 30 minutes the valve through which ethylene was admitted was closed and the reaction mixture was chilled to −80°. The reactor was then opened and about 1 ml of methanol was added to arrest the catalyst. GLC analysis showed that 15% of the butadiene had been converted to 1,4-hexadiene with a trans/cis-isomer ratio of 4.15.

I claim:

1. Method of preparing 1,4-diene of high trans-isomer content which comprises contacting ethylene with 1,3-diene of the formula $$CH_2=C(R^1)CH=CHR^2$$

or $$CH_2=CHC(R^1)=CHR^2$$

where
$R^1$ is hydrogen, methyl, ethyl or chlorine, and
$R^2$ is hydrogen, $C_1$–$C_{15}$ alkyl, $C_6$–$C_{12}$ aryl, or $C_7$–$C_{18}$ alkaryl,
in the presence of a catalyst system which comprises
 a. organic solvent-soluble organonickel compound in which the nickel is zerovalent or divalent,
 b. hydrocarbylaluminum halide selected from the group consisting of hydrocarbylaluminum chlorides and hydrocarbylaluminum bromides, and
 c. aryl phosphinite of the formula $R^3R^4POR^5$ where
- $R^3$ and $R^4$, alike or different, are phenyl, or substituted phenyl containing up to two substituents selected from the group consisting of $C_1$–$C_6$ alkyl, chlorine, fluorine, bromine and iodine, and
- $R^5$ is $C_6$–$C_{12}$ aryl or substituted $C_6$–$C_{12}$ aryl containing up to two substituents selected from the group consisting of $C_1$–$C_6$ alkyl, $C_1$–$C_6$ alkoxy, chlorine, bromine, iodine, fluorine, trifluoromethyl and di($C_1$–$C_6$ alkyl) amino.

2. The method of claim 1 in which the catalyst system also contains a heteroorganoaluminum compound of the formula $(R^6)_aAlZ_b$ where
- $R^6$ is $C_1$–$C_6$ alkyl, $C_3$–$C_6$ cycloalkyl, $C_7$–$C_{18}$ aralkyl, or $C_6$–$C_{12}$ aryl,
- Z is $OR^7$, $-NR^8(R^9)$, or $=NR^{10}$ where
- $R^7$, $R^8$, $R^9$ and $R^{10}$, alike or different, are $C_1$–$C_6$ alkyl, $C_3$–$C_6$ cycloalkyl, $C_7$–18 aralkyl, or $C_6$–$C_{12}$ aryl,
- $a$ is 1 or 2,
- $b$ is 1 or 2, and
- $a + b$ is 3, except that when Z is $=NR^{10}$,
- $a$ is 1,
- $b$ is 1,
- $a + b$ is 2, and
- $R^6$ can also be hydrogen.

3. Method of preparing 1,4-diene of high trans-isomer content which comprises contacting ethylene with 1,3-diene of the formula $CH_2=C(R^1)CH=CHR^2$ or $CH_2=CHC(R^1)=CHR^2$ where
- $R^1$ is hydrogen, methyl or ethyl, and
- $R^2$ is hydrogen or $C_1$–$C_{15}$ alkyl, in the presence of a catalyst system which comprises
a. organic solvent-soluble organonickel compound in which the nickel is zerovalent or divalent,
b. hydrocarbylaluminum halide selected from the group consisting of hydrocarbylaluminum chlorides and hydrocarbylaluminum bromides, and
c. aryl phosphinite of the formula $R^3R^4POR^5$ where
- $R^3$ and $R^4$, alike or different, are phenyl, or substituted phenyl containing up to two substituents selected from the group consisting of $C_1$–$C_6$ alkyl, chlorine, fluorine, bromine and iodine, and
- $R^5$ is $C_6$–$C_{12}$ aryl, or substituted $C_6$–$C_{12}$ aryl containing up to two substituents selected from the group consisting of $C_1$–$C_6$ alkyl, $C_1$–$C_6$ alkoxy, chlorine, bromine, iodine, fluorine, trifluoromethyl and di($C_1$–$C_6$ alkyl)amino.

4. The method of claim 3 in which the 1,3-diene is 1,3-butadiene.

5. The method of claim 4 in which the hydrocarbylaluminum halide is alkylaluminum dihalide.

6. The method of claim 5 in which the aryl phosphinite is a substituted phenyl diphenylphosphinite.

7. The method of claim 6 in which the organonickel compound is nickel(O)bis(cyclooctadiene).

8. The method of claim 3 in which the catalyst system also contains a heteroorganoaluminum compound of the formula $(R^6)_aAlZ_b$ where
- $R^6$ is $C_1$–$C_6$ alkyl, $C_3$–$C_6$ cycloalkyl, $C_7$–$C_{18}$ aralkyl, or $C_6$–$C_{12}$ aryl,
- Z is $OR^7$, $-NR^8(R^9)$, or $=NR^{10}$ where
- $R^7$, $R^8$, $R^9$ and $R^{10}$, alike or different, are $C_1$–$C_6$ alkyl, $C_3$–$C_6$ cycloalkyl, $C_7$–18 aralkyl, or $C_6$–$C_{12}$ aryl,
- $a$ is 1 or 2,
- $b$ is 1 or 2, and
- $a + b$ is 3, except that when Z is $=NR^{10}$,
- $a$ is 1,
- $b$ is 1,
- $a + b$ is 2, and
- $R^6$ can also be hydrogen.

9. The method of claim 8 in which the 1,3-diene is 1,3-butadiene.

10. The method of claim 9 in which the hydrocarbylaluminum halide is alkylaluminum dihalide.

11. The method of claim 10 in which the aryl phosphinite is a substituted phenyl diphenylphosphinite.

12. The method of claim 11 in which the organonickel compound is nickel(O)bis(cyclooctadiene).

* * * * *

UNITED STATES PATENT OFFICE
CERTIFICATE OF CORRECTION

PATENT NO. : 4,025,570
DATED : May 24, 1977
INVENTOR(S) : Richard David Cramer

It is certified that error appears in the above-identified patent and that said Letters Patent are hereby corrected as shown below:

Column 1, line 60, "$(R_1)AlZ_b$" should read --$(R_1)_a AlZ_b$--

Column 3, line 45, "4-phenyl-1,3-butadiene, and" should read --4-phenyl-1,3-butadiene, 4-naphthyl-1,3-butadiene, 4-(4-tolyl)-1,3-butadiene, and--.

Column 4, line 3, "1,5-cyclo-octadiene" should read --1,5-cyclooctadiene--.

Column 7, line 21, "ratio" should read --rate--.

Column 8, line 2, "use" should read --used--.

Signed and Sealed this

Thirteenth Day of December 1977

[SEAL]

Attest:

RUTH C. MASON
Attesting Officer

LUTRELLE F. PARKER
Acting Commissioner of Patents and Trademarks